US009255190B2

(12) United States Patent
Plochinger et al.

(10) Patent No.: US 9,255,190 B2
(45) Date of Patent: Feb. 9, 2016

(54) PROCESS FOR THE CONTINUOUS PREPARATION OF WATER-ABSORBENT POLYMERS

(71) Applicants: Harald Plochinger, Buhl (DE); Daniel Fricker, Roeschwoog (FR); Richard Walther, Rheinmunster (DE); Marc Hager, Haguenau (FR)

(72) Inventors: Harald Plochinger, Buhl (DE); Daniel Fricker, Roeschwoog (FR); Richard Walther, Rheinmunster (DE); Marc Hager, Haguenau (FR)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 14/364,525

(22) PCT Filed: Dec. 14, 2012

(86) PCT No.: PCT/EP2012/075481
§ 371 (c)(1),
(2) Date: Jun. 11, 2014

(87) PCT Pub. No.: WO2013/104484
PCT Pub. Date: Jul. 18, 2013

(65) Prior Publication Data
US 2014/0323663 A1 Oct. 30, 2014

(30) Foreign Application Priority Data
Jan. 12, 2012 (EP) .................................. 12150881

(51) Int. Cl.
C08J 3/24 (2006.01)
A61L 15/22 (2006.01)
A61L 15/60 (2006.01)
C08F 6/00 (2006.01)
B01J 19/20 (2006.01)
B01J 19/22 (2006.01)
C08F 220/06 (2006.01)

(52) U.S. Cl.
CPC .. *C08J 3/24* (2013.01); *A61L 15/22* (2013.01); *A61L 15/60* (2013.01); *B01J 19/20* (2013.01); *B01J 19/22* (2013.01); *C08F 6/008* (2013.01); *C08F 220/06* (2013.01); *C08J 3/245* (2013.01); *C08J 2333/02* (2013.01)

(58) Field of Classification Search
None
See application file for complete search history.

(56) References Cited

U.S. PATENT DOCUMENTS

| | | | |
|---|---|---|---|
| 3,998,433 A | 12/1976 | Iwako | |
| 4,076,663 A | 2/1978 | Masuda et al. | |
| 4,179,367 A | 12/1979 | Barthell et al. | |
| 4,286,082 A | 8/1981 | Tsubakimoto et al. | |
| 4,587,308 A | 5/1986 | Makita et al. | |
| 4,857,610 A | 8/1989 | Chmelir et al. | |
| 4,893,999 A | 1/1990 | Chmelir et al. | |
| 5,344,230 A * | 9/1994 | Kowalczyk ....... | B01F 15/00435 366/100 |
| 5,397,507 A | 3/1995 | Bauer et al. | |
| 5,409,771 A | 4/1995 | Dahmen et al. | |
| 5,610,220 A | 3/1997 | Klimmek et al. | |
| 5,672,633 A | 9/1997 | Brehm et al. | |
| 5,712,316 A | 1/1998 | Dahmen et al. | |
| 6,620,889 B1 | 9/2003 | Mertens et al. | |
| 6,710,141 B1 | 3/2004 | Heide et al. | |
| 7,179,862 B2 | 2/2007 | Mertens et al. | |
| 7,285,599 B2 | 10/2007 | Mertens et al. | |
| 7,572,864 B2 | 8/2009 | Mertens et al. | |
| 7,851,550 B2 | 12/2010 | Kadonaga et al. | |
| 8,048,942 B2 * | 11/2011 | Fricker ................... | C08F 2/00 523/343 |
| 8,063,121 B2 | 11/2011 | Fricker et al. | |
| 8,119,755 B2 | 2/2012 | Weismantel et al. | |
| 8,198,385 B2 | 6/2012 | Gartner et al. | |
| 8,236,715 B2 | 8/2012 | Schmidt et al. | |
| 8,252,873 B1 | 8/2012 | Gartner et al. | |
| 8,287,999 B2 | 10/2012 | Schmidt et al. | |
| 8,357,766 B2 | 1/2013 | Fricker et al. | |
| 8,445,596 B2 | 5/2013 | Mertens et al. | |
| 8,653,210 B2 | 2/2014 | Fricker et al. | |
| 2004/0176544 A1 | 9/2004 | Mertens et al. | |
| 2004/0186229 A1 | 9/2004 | Heide et al. | |
| 2006/0177647 A1 | 8/2006 | Schmidt et al. | |
| 2006/0178071 A1 | 8/2006 | Schmidt et al. | |
| 2010/0010184 A1 | 1/2010 | Weismantel et al. | |
| 2011/0245436 A1 | 10/2011 | Gartner et al. | |
| 2014/0121322 A1 | 5/2014 | Fricker et al. | |

FOREIGN PATENT DOCUMENTS

| | | |
|---|---|---|
| CN | 1058609 A | 2/1992 |
| CN | 1342180 A | 3/2002 |

(Continued)

OTHER PUBLICATIONS

Buchholz, Frederick L. and Graham, Andrew T., "Modern Superabsorbent Polymer Technology," copyright 1998, John Wiley & Sons, Inc., Chapter 1: "Absorbency and Superabsorbency," pp. 1-17 (19 pages).

(Continued)

*Primary Examiner* — Robert C Boyle
(74) *Attorney, Agent, or Firm* — Smith Moore Leatherwood LLP; Philip P. McCann; John P. Zimmer

(57) ABSTRACT

The invention relates generally to a process for the preparation of water-absorbent polymer particles, including the process steps of preparing particulate water-absorbent polymer and mixing the particulate water-absorbent polymer with an aqueous crosslinker solution and heat-treating the mixture of particulate water-absorbent polymer in a horizontally operated mixing device, wherein the horizontally operated mixing device is hydraulically driven. The invention also relates to water-absorbent polymer particles obtainable by such a process.

7 Claims, 4 Drawing Sheets

(56) References Cited

FOREIGN PATENT DOCUMENTS

| | | |
|---|---|---|
| CN | 1630678 A | 6/2005 |
| CN | 101119756 A | 2/2008 |
| CN | 102089012 A | 6/2011 |
| DE | 2520788 A1 | 11/1975 |
| DE | 2617612 A1 | 11/1977 |
| DE | 2706135 A1 | 8/1978 |
| DE | 3503458 A1 | 8/1985 |
| DE | 3544770 A1 | 6/1987 |
| DE | 4020780 C1 | 8/1991 |
| DE | 4244548 A1 | 7/1994 |
| DE | 4418818 A1 | 1/1995 |
| DE | 4333056 A1 | 3/1995 |
| DE | 19909653 A1 | 9/2000 |
| DE | 10223060 A1 | 12/2003 |
| EP | 0955086 A2 | 11/1999 |
| EP | 1683813 A2 | 7/2006 |
| JP | H04-353403 A | 12/1992 |
| JP | 2008-038128 A | 2/2008 |
| WO | 0138402 A1 | 5/2001 |
| WO | 0222717 A1 | 3/2002 |
| WO | 02056812 A2 | 7/2002 |
| WO | 2006083585 B2 | 8/2006 |

OTHER PUBLICATIONS

Buchholz, Frederick L. and Graham, Andrew T., "Modern Superabsorbent Polymer Technology," copyright 1998, John Wiley & Sons, Inc., Chapter 2: "Chemistry of Superabsorbent Polyacrylates," pp. 19-67 (51 pages).

Buchholz, Frederick L. and Graham, Andrew T., "Modern Superabsorbent Polymer Technology," copyright 1998, John Wiley & Sons, Inc., Chapter 3: "Commercial Processes for the Manufacture of Superabsorbent Polymers," pp. 69-117 (51 pages).

Buchholz, Frederick L. and Graham, Andrew T., "Modern Superabsorbent Polymer Technology," copyright 1998, John Wiley & Sons, Inc., Chapter 4: "Analysis and Characterization of Superabsorbent Polymers," pp. 119-165 (49 pages).

Buchholz, Frederick L. and Graham, Andrew T., "Modern Superabsorbent Polymer Technology," copyright 1998, John Wiley & Sons, Inc., Chapter 5: "The Structure and Properties of Superabsorbent Polyacrylates," pp. 167-221 (57 pages).

Gartner et al., U.S. Appl. No. 14/358,792, filed May 16, 2014.

Gartner et al., U.S. Appl. No. 14/358,936, filed May 16, 2014.

International Search Report mailed on Apr. 10, 2013 in PCT/EP2012/075481 (4 pages).

Web page: "Nara Paddle Dryer (NPD)," Nara Machine Co., LTD, 2014, www.nara-m.co.jp/english/product/dryer/npd.html (3 pages).

Web page: "Product Preview: The new generation paddle dryer—the Boono (Nara Machinery Co., Ltd. Europa)," 2014, Forum Bulk-online, forum.bulk-online.com/showthread.php?23246-NARA-Machinery-Co (4 pages).

Written Opinion mailed on Apr. 10, 2013 in PCT/EP2012/075481 (10 pages).

* cited by examiner

PROCESS FOR THE CONTINUOUS PREPARATION OF WATER-ABSORBENT POLYMERS

This application is a national stage application under 35 U.S.C. §371 of International Application No. PCT/EP2012/075481 filed 14 Dec. 2012, which claims priority to European Application No. EP 12150881.6 filed 12 Jan. 2012, the disclosures of which are expressly incorporated herein by reference.

FIELD

The invention relates to a process for the preparation of water-absorbent polymer particles, to water-absorbent polymer particles obtainable by such a process, to a composite material, to a process for the preparation of a composite material, to the composite material obtainable by such a process, to chemical products and to the use of the water-absorbent polymer particles or a composite material.

BACKGROUND

Superabsorbers are water-insoluble, crosslinked polymers which are able to absorb large amounts of aqueous fluids, especially body fluids, more especially urine or blood, with swelling and the formation of hydrogels, and to retain such fluids under a certain pressure. By virtue of those characteristic properties, such polymers are chiefly used for incorporation into sanitary articles, such as, for example, baby's nappies/diapers, incontinence products or sanitary towels.

The preparation of superabsorbers is generally carried out by free-radical polymerisation of acid-group-carrying monomers in the presence of crosslinkers, it being possible for polymers having different absorber properties to be prepared by the choice of the monomer composition, the crosslinkers and the polymerisation conditions and of the processing conditions for the hydrogel obtained after the polymerisation (for details see, for example, *Modern Superabsorbent Polymer Technology*, F L Buchholz, G T Graham, Wiley-VCH, 1998).

The acid-group-carrying monomers can be polymerized in the presence of the crosslinkers in a batch process or in a continuous process. An example for a continuous process for preparing superabsorbers is disclosed in U.S. Pat. No. 4,857,610. According to this process, an aqueous monomer solution containing acrylic acid and crosslinkers is continuously charged in a layer at least one centimeter thick on a moving endless conveyor belt and polymerized. The gel that is thus obtained is continuously discharged from the conveyor belt and is subsequently comminuted, dried, sized and optionally surface treated.

The surface treatment of the water-absorbent polymer particles usually comprises a surface-crosslinking step, in which the polymer particles are first mixed with an aqueous solution comprising a surface-crosslinking agent and in which the thus obtained mixture is than heat-treated in a further mixing device, preferably in a horizontally operated mixing device such as an electrically driven NARA-mixer. However, in order to obtain water-absorbent polymer particles with predictable and reproducible absorption properties it is very important to control the residence time of the polymer particles in the NARA-mixer. The disadvantage of the prior art processes, however, can be seen in the fact that if the NARA-mixer has to be stopped, for example due to a certain overload or for other reasons, it is very difficult to restart the mixer in the fully loaded state, especially if the fluidity of the a moist polymer powder is decreased due to the presence of additives such as aluminium salts. In case of an electrically driven NARA-mixer the maximum torque can not be reached right from the restart of the mixer, with the result that in the initial phase of the restart the polymer particles can not be mixed sufficiently. These problems in restarting the NARA-mixer result in an unpredictable extension of the residence time of the polymer particles in the NARA-mixer and thus to unpredictable absorption properties of the end product. As the inner surfaces of the NARA-mixer are heated, the polymer particles may even inflame if they contact these surfaces for a prolonged time.

An object of the invention is to overcome at least a part of the above mentioned drawbacks of the prior art. A further object is to provide a process to prepare water-absorbent polymer particles in a time and resource efficient way. A further object of the invention is to perform the process of treating the surface of water-absorbent polymer particles, especially the process of crosslinking the surface of water-absorbent polymer particles, under more reproducible conditions. Another object is to provide a continuous process for treating the surface of water-absorbent polymer particles, especially for crosslinking the surface of water-absorbent polymer particles, which can be performed more efficiently, e.g. which can be stopped and restarted more easily. The process should also allow to homogeneously mix additives, which usually have a negative impact on the fluidity of the mixture, with water-absorbent polymer particles.

SUMMARY

A contribution to the solution of these objects is made by a process for the preparation of water-absorbent polymer particles, comprising the process steps of (i) preparing an aqueous monomer solution comprising at least partially neutralized, monoethylenically unsaturated monomers bearing carboxylic acid groups ($\alpha 1$) and at least one crosslinker ($\alpha 3$);
(ii) optionally adding fine particles of a water-absorbent polymer or aqueous salt solutions to the aqueous monomer solution;
(iii) adding a polymerization initiator or a at least one component of a polymerization initiator system that comprises two or more components to the aqueous monomer solution;
(iv) decreasing the oxygen content of the aqueous monomer solution;
(v) charging the aqueous monomer solution into a polymerization reactor;
(vi) polymerizing the monomers in the aqueous monomer solution in the polymerization reactor;
(vii) discharging the polymer gel strand out of the polymerization reactor and optionally comminuting the polymer gel thereby obtaining polymer gel particles;
(viii) drying the polymer gel particles;
(ix) grinding the dried polymer gel particles thereby obtaining particulate water-absorbent polymer particles;
(x) sizing the grinded water-absorbent polymer particles; and
(xi) crosslinking the surface of the grinded and sized water-absorbent polymer particles;

wherein process step (xi) comprises the steps of:

DETAILED DESCRIPTION (x1a) mixing the particles with an aqueous crosslinker solution; and
(x2a) heat-treating the mixture obtained in process step (x1a) in a horizontally operated mixing device;

wherein the horizontally operated mixing device is hydraulically driven.

The process according to the present invention is preferably a continuous process in which the aqueous monomer solution is continuously provided and is continuously fed into the polymerization reactor. The hydrogel obtained is continuously discharged out of the polymerization reactor and is continuously comminuted, dried, grinded and classified in the subsequent process steps. This continuous process may, however, be interrupted in order to, for example, substitute certain parts of the process equipment, like the belt material of the conveyor belt if a conveyor belt is used as the polymerization reactor, clean certain parts of the process equipment, especially for the purpose of removing polymer deposits in tanks or pipes, or start a new process when water-absorbent polymer particles with other absorption characteristics have to be prepared.

Water-absorbent polymer particles which are preferred according to the invention are particles that have an average particle size in accordance with WSP 220.2 (test method of "*Word Strategic Partners*" EDANA and INDA) in the range of from 10 to 3,000 µm, preferably 20 to 2,000 µm and particularly preferably 150 to 850 µm. In this context, it is particularly preferable for the content of polymer particles having a particle size in a range of from 300 to 600 µm to be at least 30 wt.-%, particularly preferably at least 40 wt.-% and most preferably at least 50 wt.-%, based on the total weight of the water-absorbent polymer particles.

In process step (i) of the process according to the present invention an aqueous monomer solution containing partially neutralized, monoethylenically unsaturated monomers bearing carboxylic acid groups ($\alpha$1) and at least one crosslinker ($\alpha$3) is prepared.

Preferred monoethylenically unsaturated monomers bearing carboxylic acid groups ($\alpha$1) are those cited in DE 102 23 060 A1 as preferred monomers ($\alpha$1), whereby acrylic acid is particularly preferred.

It is preferred according to the present invention that the water-absorbent polymer produced by the process according to the invention comprises monomers bearing carboxylic acid groups to at least 50 wt. %, preferably to at least 70 wt. % and further preferably to at least 90 wt. %, based on the dry weight. It is particularly preferred according to the invention, that the water-absorbent polymer produced by the process according to the invention is formed from at least 50 wt. %, preferably at least 70 wt. % of acrylic acid, which is preferably neutralized to at least 20 mol %, particularly preferably to at least 50 mol %. The concentration of the partially neutralized, monoethylenically unsaturated monomers bearing carboxylic acid groups ($\alpha$1) in the aqueous monomer solution that is provided in process step (i) is preferably in the range between 10-60 wt.-%, preferably 20 to 50 wt.-% and most preferably between 30 to 40 wt.-%, based on the total weight of the aqueous monomer solution.

The aqueous monomer solution may also comprise monoethylenically unsaturated monomers ($\alpha$2) which are copolymerizable with ($\alpha$1). Preferred monomers ($\alpha$2) are those monomers which are cited in DE 102 23 060 A1 as preferred monomers ($\alpha$2), whereby acrylamide is particularly preferred.

Preferred crosslinkers ($\alpha$3) according to the present invention are compounds which have at least two ethylenically unsaturated groups in one molecule (crosslinker class I), compounds which have at least two functional groups which can react with functional groups of the monomers ($\alpha$1) or ($\alpha$2) in a condensation reaction (=condensation crosslinkers), in an addition reaction or a ring-opening reaction (crosslinker class II), compounds which have at least one ethylenically unsaturated group and at least one functional group which can react with functional groups of the monomers ($\alpha$1) or ($\alpha$2) in a condensation reaction, an addition reaction or a ring-opening reaction (crosslinker class III), or polyvalent metal cations (cross-linker class IV). Thus with the compounds of crosslinker class I a crosslinking of the polymer is achieved by radical polymerisation of the ethylenically unsaturated groups of the crosslinker molecules with the monoethylenically unsaturated monomers ($\alpha$1) or ($\alpha$2), while with the compounds of crosslinker class II and the polyvalent metal cations of crosslinker class IV a crosslinking of the polymer is achieved respectively via condensation reaction of the functional groups (crosslinker class II) or via electrostatic interaction of the polyvalent metal cation (crosslinker class IV) with the functional groups of the monomer ($\alpha$1) or ($\alpha$2). With compounds of cross-linker class III a cross-linking of the polymers is achieved correspondingly by radical polymerisation of the ethylenically unsaturated groups as well as by condensation reaction between the functional groups of the cross-linkers and the functional groups of the monomers ($\alpha$1) or ($\alpha$2).

Preferred crosslinkers ($\alpha$3) are all those compounds which are cited in DE 102 23 060 A1 as crosslinkers ($\alpha$3) of the crosslinker classes I, II, III and IV, whereby as compounds of crosslinker class I, N,N'-methylene bisacrylamide, polyethyleneglycol di(meth)acrylates, triallylmethylammonium chloride, tetraallylammonium chloride and allylnonaethyleneglycol acrylate produced with 9 mol ethylene oxide per mol acrylic acid are particularly preferred, and and as compounds of crosslinker class IV, $Al_2(SO_4)_3$ and its hydrates are particularly preferred.

Preferred water-absorbent polymers produced by the process according to the invention are polymers which are crosslinked by crosslinkers of the following crosslinker classes or by crosslinkers of the following combinations of crosslinker classes respectively: I, II, III, IV, I II, I III, I IV, I II III, I II IV, I III IV, II III IV, II IV or III IV.

Further preferred water-absorbent polymers produced by the process according to the invention are polymers which are crosslinked by any of the crosslinkers disclosed in DE 102 23 060 A1 as crosslinkers of crosslinker classes I, whereby N,N'-methylene bisacrylamide, polyethyleneglycol di(meth)acrylates, triallyl-methylammonium chloride, tetraallylammonium chloride and allylnonaethylene-glycol acrylate produced from 9 mol ethylene oxide per mol acrylic acid are particularly preferred as crosslinkers of crosslinker class I.

The aqueous monomer solution may further comprise water-soluble polymers ($\alpha$4). Preferred water-soluble polymers ($\alpha$4) include partly or completely saponified polyvinyl alcohol, polyvinylpyrrolidone, starch or starch derivatives, polyglycols or polyacrylic acid. The molecular weight of these polymers is not critical, as long as they are water-soluble. Preferred water-soluble polymers ($\alpha$4) are starch or starch derivatives or polyvinyl alcohol. The water-soluble polymers ($\alpha$4), preferably synthetic, such as polyvinyl alcohol, can not only serve as a graft base for the monomers to be polymerized. It is also conceivable for these water-soluble polymers to be mixed with the hydrogel or the already dried, water-absorbent polymer.

The aqueous monomer solution can furthermore also comprise auxiliary substances ($\alpha$5), these auxiliary substances including, in particular, complexing agents, such as, for example, EDTA.

The relative amount of monomers (α1) and (α2) and of crosslinking agents (α3) and water-soluble polymers (α4) and auxiliary substances (α5) in the aqueous monomer solution is preferably chosen such that the water-absorbent polymer structure obtained in process step x) after drying is based to the extent of 20-99.999 wt.-%, preferably to the extent of 55-98.99 wt.-% and particularly preferably to the extent of 70-98.79 wt.-% on monomers (α1), to the extent of 0-80 wt.-%, preferably to the extent of 0-44.99 wt.-% and particularly preferably to the extent of 0.1-44.89 wt.-% on the monomers (α2), to the extent of 0-5 wt.-%, preferably to the extent of 0.001-3 wt.-% and particularly preferably to the extent of 0.01-2.5 wt.-% on the crosslinking agents (α3), to the extent of 0-30 wt.-%, preferably to the extent of 0-5 wt.-% and particularly preferably to the extent of 0.1-5 wt.-% on the water-soluble polymers (α4), to the extent of 0-20 wt.-%, preferably to the extent of 0-10 wt.-% and particularly preferably to the extent of 0.1-8 wt.-% on the auxiliary substances (α5), and to the extent of 0.5-25 wt.-%, preferably to the extent of 1-10 wt.-% and particularly preferably to the extent of 3-7 wt.-% on water (α6)

the sum of the amounts by weight (α1) to (α6) being 100 wt.-%.

Optimum values for the concentration in particular of the monomers, crosslinking agents and water-soluble polymers in the monomer solution can be determined by simple preliminary experiments or from the prior art, in particular the publications U.S. Pat. No. 4,286,082, DE 27 06 135 A1, U.S. Pat. No. 4,076,663, DE 35 03 458 A1, DE 40 20 780 C1, DE 42 44 548 A1, DE 43 33 056 A1 and DE 44 18 818 A1.

In process step (ii) fine particles of a water-absorbent polymer or aqueous salt solutions may optionally be added to the aqueous monomer solution.

Water-absorbent fine particles are preferably water-absorbent polymer particles the composition of which corresponds to the composition of the above described water-absorbent polymer particles, wherein it is preferred that at least 90 wt.-% of the water-absorbent fine particles, preferably at least 95 wt.-% of the water-absorbent fine particles and most preferred at least 99 wt.-% of the water-absorbent polymer particles have a particle size of less than 200 μm, preferably less than 150 μm and particular preferably less than 100 μm. The water-absorbent fine particles may also comprise metal salts, in particular aluminium salts.

In a preferred embodiment of the process according to the present invention the water-absorbent fine particles which may optionally be added to the aqueous monomer solution in process step (ii) are fine particles which are obtained in process step (x) of the process according to the present invention and which are thus recycled.

The fine particles can be added to the aqueous monomer solution by means of any mixing device the person skilled of the art would consider as appropriate for this purpose. In a preferred embodiment of the present invention, which is especially useful if the process is performed continuously as described above, the fine particles are added to the aqueous monomer solution in a mixing device in which a first stream of the fine particles and a second stream of the aqueous monomer solution are directed continuously, but from different directions, onto a rotating mixing device. Such a kind of mixing setup can be realised in a so called "Rotor Stator Mixer" which comprise in their mixing area a preferably cylindrically shaped, non-rotating stator, in the centre of which a likewise preferably cylindrically shaped rotor is rotating. The walls of the rotor as well as the walls of the stator are usually provided with notches, for example notches in the form of slots, through which the mixture of fine particles and aqueous monomer solution can be sucked through and thus can be subjected to high shear forces.

In this context it is particularly preferred that the first stream of the fine particles an the second stream of the aqueous monomer solution form an angle δ in the range from 60 bis 120°, more preferred in the range from 75 bis 105°, even more preferably in the range from 85 bis 95° and most preferred from an angle of about 90°. It is also preferred that the stream of the mixture of fine particles and aqueous monomer solution that leaves the mixer and the first stream of fine particles that enters the mixer form an angle ε in the range from 60 bis 120°, preferably in the range from 75 bis 105°, even more preferred in the range from 85 bis 95° and most preferred form an angle of about 90°.

Such a kind of mixing set up can, for example, be realized by means of mixing devices which are disclosed in DE-A-25 20 788 and DE-A-26 17 612, the content of which is incorporated herein by reference. Concrete examples of mixing devices which can be used to add the fine particles to the aqueous monomer solution in process step (ii) of the present invention are the mixing devices which can be obtained by the IKA® Werke GmbH & Co. KG, Staufen, Germany, under designations MHD 2000/4, MHD 2000/05, MHD 2000/10, MDH 2000/20, MHD 2000/30 and MHD 2000/50, wherein the mixing device MHD 2000/20 is particularly preferred. Further mixing devices which can be used are those offered by ystral GmbH, Ballrechten-Dottingen, Germany, for example under designation "Conti TDS", or by Kinematika AG, Luttau, Switzerland, for example under the trademark Megatron®.

The amount of fine particles that may be added to the aqueous monomer solution in process step (ii) is preferably in the range from 0.1 to 15 wt.-%, even more preferred in the range from 0.5 to 10 wt.-% Gew.-% and most preferred in the range from 3 to 8 wt.-%, based in the weight of the aqueous monomer solution.

As an aqueous salt solution that may be added to the aqueous monomer solution in process step (ii) aqueous solutions containing carbonate salts can be used. Such solutions can be obtained as a so called "scrubber water", as disclosed in US 2011/0245436 A1

In process step (iii) of the process according to the present invention a polymerization initiator or at least one component of a polymerization initiator system that comprises two or more components is added to the aqueous monomer solution.

As polymerization initiators for initiation of the polymerisation all initiators forming radicals under the polymerisation conditions can be used, which are commonly used in the production of superabsorbers. Among these belong thermal catalysts, redox catalysts and photo-initiators, whose activation occurs by energetic irradiation. The polymerisation initiators may be dissolved or dispersed in the aqueous monomer solution. The use of water-soluble catalysts is preferred.

As thermal initiators may be used all compounds known to the person skilled in the art that decompose under the effect of temperature to form radicals. Particularly preferred are thermal polymerisation initiators with a half life of less than 10 seconds, more preferably less than 5 seconds at less that 180° C., more preferably at less than 140° C. Peroxides, hyperoxides, hydrogen peroxide, persulfates and azo compounds are particularly preferred thermal polymerisation initiators. In some cases it is advantageous to use mixtures of various thermal polymerisation initiators. Among such mixtures, those consisting of hydrogen peroxide and sodium or potassium peroxodisulfate are preferred, which may be used in any desired quantitative ratio. Suitable organic peroxides are preferably acetylacetone peroxide, methyl ethyl ketone peroxide, benzoyl peroxide, lauroyl peroxide, acetyl peroxide, capryl peroxide, isopropyl peroxidicarbonate, 2-ethylhexyle peroxidicarbonate, tert.-butyl hydroperoxide, cumene hydroperoxide, tert.-amyl perpivalate, tert.-butyl perpivalate, tert.-butyl perneohexonate, tert.-butyl isobutyrate, tert.-butyl per-2-ethylhexenoate, tert.-butyl perisononanoate, tert.-butyl permaleate, tert.-butyl perbenzoate, tert.-butyl-3,5,5-trimethylhexanoate and amyl perneodecanoate. Furthermore, the following thermal polymerisation initiators are preferred: azo compounds such as azo-bis-isobutyronitrol, azo-bis-dimethylvaleronitril, 2,2-azobis-(2-amidinopropane)dihydrochloride, azo-bis-ami-dinopropane dihydrochloride, 2,2'-azobis-(N,N-dimethylene)isobutyramidine di-hydrochloride, 2-(carbamoylazo)isobutyronitrile and 4,4'-azobis-(4-cyanovaleric acid). The aforementioned compounds are used in conventional amounts, preferably in a range from 0.01 to 5, more preferably 0.1 to 2 mol %, respectively based upon the amount of the monomers to be polymerised.

Redox catalyst comprise two of more components, usually one or more of the peroxo compounds listed above, and at least one reducing component, preferably ascorbic acid, glucose, sorbose, mannose, ammonium or alkali metal hydrogen sulfite, sulfate, thiosulfate, hyposulfite or sulfide, metal salts such as iron II ions or silver ions or sodium hydroxymethyl sulfoxylate. Preferably ascorbic acid or sodium pyrosulfite is used as reducing component of the redox catalyst. $1 \times 10^{-5}$ to 1 mol % of the reducing component of the redox catalyst and $1 \times 10^{-5}$ to 5 mol % of the oxidising component of the redox catalyst are used, in each case referred to the amount of monomers used in the polymerisation. Instead of the oxidising component of the redox catalyst, or as a complement thereto, one or more, preferably water-soluble azo compounds may be used.

If the polymerisation is initiated by action of energetic beams, so-called photo-initiators are generally used as initiator. These can comprise for example so-called α-splitters, H-abstracting systems or also azides. Examples of such initiators are benzophenone derivatives such as Michlers ketone, phenanthrene derivatives, fluorine derivatives, anthraquinone derivatives, thioxanthone derivatives, cumarin derivatives, benzoinether and derivatives thereof, azo compounds such as the above-mentioned radical formers, substituted hexaarylbisimidazoles or acylphosphine oxides. Examples of azides are: 2-(N,N-dimethylamino)ethyl-4-azidocinnamate, 2-(N,N-dimethylamino)ethyl-4-azidonaphthylketone, 2-(N,N-dimethylamino)ethyl-4-azidobenzoate, 5-azido-1-naphthyl-2'-(N,N-dimethylamino)ethylsulfone, N-(4-sulfonylazidophenyl)maleinimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis(p-azidobenzylidene)-4-methylcyclohexanone. The photo-initiators, when used, are generally employed in quantities from 0.01 to 5 wt.-% based on the monomers to be polymerised.

A particularly preferred redox system that is used in the process according to the present invention is a redox system comprising hydrogen peroxide, sodium peroxodisulfate and ascorbic acid.

In this context it should also be noted that the polymerization initiator may be added before, during or after process step (iv), i.e. after the oxygen content of the aqueous monomer solution has been decreased. If a polymerisation initiator system is used that comprises two or more components, like the preferred initiator system that comprises hydrogen peroxide, sodium peroxodisulfate and ascorbic acid and that is active only if all the components have been added, one or more of the components of such a polymerisation initiator system may, for example, be added before process step (iv), whereas the remaining component or the remaining components which are necessary to complete the activity of the polymerisation initiator system, are added after process step (iv), perhaps even after process step (v).

In process step (iv) of the process according to the present invention the oxygen content of the aqueous monomer solution is decreased, whereby it should be mentioned that process step (iv) can also be performed before, during or after process step (ii). Preferably, the oxygen content of the aqueous monomer solution is decreased after the fine particles have been added in process step (ii).

The oxygen content of the aqueous monomer solution is decreased by bringing the aqueous monomer solution into contact with an inert gas, such as nitrogen. The phase of the inert gas being in contact with the aqueous monomer solution is free of oxygen and is thus characterized by a very low oxygen partial pressure. As a consequence oxygen converts from the aqueous monomer solution into the phase of the inert gas until the oxygen partial pressures in the phase of the inert gas and the aqueous monomer solution are equal. Bringing the aqueous monomer phase into contact with a phase of an inert gas can be accomplished, for example, by introducing bubbles of the inert gas into the monomer solution in cocurrent, countercurrent or intermediate angles of entry. Good mixing can be achieved, for example, with nozzles, static or dynamic mixers or bubble columns. The oxygen content of the monomer solution before the polymerization is preferably lowered to less than 1 ppm by weight, more preferably to less than 0.5 ppm by weight.

In process step (v) of the process according to the present invention the aqueous monomer solution is charged into a polymerization reactor, preferably onto a conveyor belt, especially preferred at an upstream position of the conveyor belt and in process step (vi) the monomers in the aqueous monomer solution are polymerized in the polymerization reactor, thereby obtaining a polymer gel. If polymerization is performed on a polymerization belt as the polymerization reactor, a polymer gel strand is obtained in a downstream portion of the conveyor belt, which, before drying, is preferably comminuted in order to obtain gel particles.

As the polymerization reactor every reactor can be used which the person skilled in the art would regard as appropriate for the continuous or batchwise polymerization of monomers like acrylic acid in aqueous solutions. An example of a suitable polymerization reactor is a kneading reactor. In a kneader the polymer gel formed in the polymerization of the aqueous monomer solution is comminuted continuously by, for example, contrarotatory stirrer shafts, as described in WO 2001/38402.

Another example of a preferred polymerization reactor is a conveyor belt. As a conveyor belt that is useful for the process according to the present invention any conveyor belt can be used which the person skilled in the art considers to be useful as a support material onto which the above described aqueous monomer solution can be charged and subsequently polymerized to form a hydrogel. Examples of conveyor belts which can be used in the process according to the present invention are disclosed in DE-A-35 44 770, EP-A-0 955 086 and EP-A-1 683 813, the disclosure of which is incorporated herein by reference.

The conveyor belt usually comprises an endless moving conveyor belt passing over supporting elements and at least two guide rollers, of which at least one is driven and one is configured so as to be adjustable. Optionally, a winding and feed system for a release sheet that may be used in sections on the upper surface of the conveyor belt is provided. The system includes a supply and metering system for the reaction components, and optional irradiating means arranged in the direction of movement of the conveyor belt after the supply and metering system, together with cooling and heating devices, and a removal system for the polymer gel strand that is arranged in the vicinity of the guide roller for the return run of the conveyor belt. In order to provide for the completion of polymerization with the highest possible space-time yield, according to the present invention, in the vicinity of the upper run of the conveyor belt on both sides of the horizontal supporting elements, starting in the area of the supply and metering systems, there are upwardly extending supporting elements, the longitudinal axes of which intersect at a point that is beneath the upper run, and which shape the conveyor belt that is supported by them so that it become suitably trough-shaped. Thus, according to the present invention, the conveyor belt is supported in the vicinity of the supply system for the reaction components by a plurality of trough-shaped supporting and bearing elements that form a deep trough-like or dish-like configuration for the reaction components that are introduced. The desired trough-like shape is determined by the shape and arrangement of the supporting elements along the length of the path of the upper run. In the area where the reaction components are introduced, the supporting elements should be relatively close to each other, whereas in the subsequent area, after the polymerization has been initiated, the supporting elements can be arranged somewhat further apart. Both the angle of inclination of the supporting elements and the cross-section of the supporting elements can be varied in order to flatten out the initially deep trough towards the end of the polymerization section and once again bring it to an extended state. In a further embodiment of the invention, each supporting element is preferably formed by a cylindrical or spherical roller that is rotatable about its longitudinal axis. By varying both the cross-section of the roller as well as the configuration of the roller it is easy to achieve the desired cross-sectional shape of the trough. In order to ensure proper formation of the trough by the conveyor belt, both when it makes the transition from a flat to a trough-like shape and when it is once again returned to the flat shape, a conveyor belt that is flexible in both the longitudinal and the transverse directions is preferred.

In process step (vii) of the process according to the present invention the particulate polymer gel that is obtained in the polymerization reactor, preferably the polymer gel particles obtained in the kneading reactor or the polymer gel strand obtained in the downstream portion of the conveyor belt, is/are discharged out of the reactor and is/are, especially in the case of the polymer gel strand obtained on the conveyor belt, (further) comminuted, thereby obtaining polymer gel particles. Preferably, the resulting polymer gel strand is removed from the conveyor belt as a continuous strand that is of a soft semi-solid consistency and is then passed on for further processing such as comminution.

Comminution of the polymer gel strand is preferably performed in at least three steps:

in a first step, a cutting unit, preferably a knife, for example a knife as disclosed in WO-A-96/36464, is used for cutting the polymer gel strand into flat gel strips, preferably with a length within the range of 5 to 500 mm, preferably from 10 to 300 mm and particularly preferably from 100 to 200 mm, a height within the range from 1 to 30 mm, preferably from 5 to 25 mm and particularly preferably from 10 to 20 mm as well as a width within the range from 1 to 500 mm, preferably from 5 to 250 mm and particularly preferably from 10 to 200 mm;

in a second step, a shredding unit, preferably a breaker, is used for shredding the gel strips into gel pieces, preferably with a length within the range of 2.5 to 25 mm, preferably from 1 to 12.5 mm, a height within the range from 0.5 to 15 mm, preferably from 0.25 to 7.5 mm as well as a width within the range from 0.5 to 20 mm, preferably from 0.25 to 10 mm and in a third step a "wolf" (grinding) unit, preferably a wolf, preferably having a screw and a whole plate, whereby the screw conveys against the whole plate is used in order to grind and crush gel pieces into polymer gel particles which are preferably smaller than the gel pieces.

An optimal surface-volume ratio is achieved hereby, which has an advantageous effect on the drying behaviour in process step (viii). A gel which has been comminuted in this way is particularly suited to belt drying. The three-step comminution offers a better "airability" because of the air channels located between the granulate kernels.

In process step (viii) of the process according to the present invention the polymer gel particles are dried.

The drying of the polymer gel particles can be effected in any dryer or oven the person skilled in the art considers as appropriate for drying the above described gel particles. Rotary tube furnaces, fluidised bed dryers, plate dryers, paddle dryers and infrared dryers may be mentioned by way of example.

Especially preferred are belt driers. A belt dryer is a convective system of drying, for the particularly gentle treatment of through-airable products. The product to be dried is placed onto an endless conveyor belt which lets gas through, and is subjected to the flow of a heated gas stream, preferably air. The drying gas is recirculated in order that it may become very highly saturated in the course of repeated passage through the product layer. A certain fraction of the drying gas, preferably not less than 10%, more preferably not less than 15% and most preferably not less than 20% and preferably up to 50%, more preferably up to 40% and most preferably up to 30% of the gas quantity per pass, leaves the dryer as a highly saturated vapor and carries off the water quantity evaporated from the product. The temperature of the heated gas stream is preferably not less than 50° C., more preferably not less than 100° C. and most preferably not less than 150° C. and preferably up to 250° C., more preferably up to 220° C. and most preferably up to 200° C.

The size and design of the dryers depends on the product to be processed, the manufacturing capacity and the drying duty. A belt dryer can be embodied as a single-belt, multi-belt, multistage or multistory system. The present invention is preferably practiced using a belt dryer having at least one belt. One-belt dryers are very particularly preferred. To ensure optimum performance of the belt-drying operation, the drying properties of the water-absorbent polymers are individually determined as a function of the processing parameters chosen. The hole size and mesh size of the belt is conformed to the product. Similarly, certain surface enhancements, such as electropolishing or Teflonizing, are possible.

The polymer gel particles to be dried are preferably applied to the belt of the belt dryer by means of a swivel belt. The feed height, i.e., the vertical distance between the swivel belt and the belt of the belt dryer, is preferably not less than 10 cm, more preferably not less than 20 cm and most preferably not less than 30 cm and preferably up to 200 cm, more preferably up to 120 cm and most preferably up to 40 cm. The thickness on the belt dryer of the polymer gel particles to be dried is preferably not less than 2 cm, more preferably not less than 5 cm and most preferably not less than 8 cm and preferably not more than 20 cm, more preferably not more than 15 cm and most preferably not more than 12 cm. The belt speed of the belt dryer is preferably not less than 0.005 m/s, more preferably not less than 0.01 m/s and most preferably not less than 0.015 m/s and preferably up to 0.05 m/s, more preferably up to 0.03 m/s and most preferably up to 0.025 m/s.

Furthermore, it is preferable according to the invention that the polymer gel particles are dried to a water content of from 0.5-25 wt.-%, preferably 1-10 wt.-% and particularly preferably 3-7 wt.-%.

In process step (ix) of the process according to the present invention the dried polymer gel particles are ground thereby obtaining particulate water-absorbent polymer particles.

For grinding of the dried polymer gel particles any device can be used the person skilled in the art considers as appropriate for grinding the above described dried polymer particles. As an example for a suitable grinding device a single- or multistage roll mill, preferably a two- or three-stage roll mill, a pin mill, a hammer mill or a vibratory mill may be mentioned.

In process step (x) of the process according to the present invention the ground water-absorbent polymer particles are sized, preferably using appropriate sieves. In this context it is particularly preferred that after sizing the water-absorbent polymer particles the content of polymer particles having a particle size of less than 150 µm is less than 10 wt.-%, preferably less than 8 wt.-% and particularly less than 6 wt.-% and that the content of polymer particles having a particle size of more than 850 µm is also less than 10 wt.-%, preferably less than 8 wt.-% and particularly less than 6 wt.-%. It is also preferred that after sizing the water-absorbent polymer particles at least 30 wt.-%, more preferred at least 40 wt.-% and most preferred at least 50 wt.-%, based on the total weight of the water-absorbent polymer particles, of the particles have a particle size in a range of from 300 to 600 µm.

In process step (xi) of the process according to the present invention the surface of the ground and sized water-absorbent polymer particles is crosslinked. As measures to crosslink the surface of water-absorbent polymer particles any measure can be used the person skilled in the art considers as appropriate for such a purpose. Preferably, the components used to treat the surface of the polymer particles (cross-linker, water soluble salts) are added in the form of aqueous solutions to the water-absorbent polymer particles. After the particles have been mixed with the aqueous solutions, they are heated to a temperature in the range from 150 to 230° C., preferably 160 to 200° C. in order to promote the surface-crosslinking reaction.

The process according to the present invention is characterized in that process step (xi) comprises the steps of:
(x1a) mixing the particles with an aqueous crosslinker solution; and
(x2a) heat-treating the mixture obtained in process step (x1a) in a horizontally operated mixing device;
wherein the horizontally operated mixing device is hydraulically driven.

The expression "horizontally operated mixing device" as used herein describes a mixing device wherein the rotational axis (i.e. the axis of rotation of the rotating parts of the mixing device) is substantially parallel to the ground and wherein the mixture is transported within the mixer in a direction parallel to the rotation axis. However, the axis might also be tilt in an angel of up to ±10 degree, preferably up to ±5 degree relative to the ground.

In order to crosslink the water-absorbent polymer particles after grinding and sizing the particles are mixed with an aqueous crosslinker solution. The aqueous crosslinker solution comprises, besides water as the solvent, a surface crosslinking agent, for example an alkylene carbonate such es ethylene carbonate, a polyol such as glycerol, or an epoxide such as ethyleneglycol diglycidylether, and optionally further additives, such as aluminium salts, in particular aluminium sulfate and/or aluminium lactate. In this context it is preferred, that the amount of water that is used in process step (x1a) is not more than 16 wt.-%, preferably not more than 12 wt.-% and most preferred not more than 8 wt.-%, based on the weight of the water-absorbent polymer particles. An appropriate mixing is reached when at least 50 vol.-%, preferred at least 70 vol.-%, more preferred at least 90 vol.-% of the water-absorbent polymer particles come into contact with the aqueous crosslinker solution during the mixing in process step (x1a).

Preferably, mixing of the water-absorbent polymer particles with the crosslinker solution can be performed in a mixing device that is different from the horizontally operated mixing device used in process step (x2a) or mixing can be performed in the horizontally operated mixing device used in process step (x2a). However, it is preferred to use a mixing device that is different from the horizontally operated mixing device used in process step (x2a). This mixing device is subsequently called "the first mixing device" in order to distinguish it from the horizontally operated mixing device used in process step (x2a). An example of a suitable first mixing device is a so-called "Schugi"-mixer.

The first mixing device as well as the horizontally operated mixing device might be operated continuously, which means that both mixing devices have a product inlet into which continuously water-absorbent polymer particles (in case of the first mixing device) or the mixture obtained in process step (x1a) (in case of the horizontally operated mixing device) are introduced and a product outlet out of which the mixture obtained in process step (x1a) (in case of the first mixing device) or the heat-treated water-absorbent polymer particles (in case of the horizontally operated mixing device) can leave the mixing device.

The horizontally operated mixing device might be part of the first mixing device. For example the horizontally operated mixing device can be connected directly or indirectly with the first mixing device. A connection might be established by means that are part of the first mixing device or the horizontally operated mixing device, for example a conveyor belt expanding at least from the first mixing device to the horizontally operated mixture device. It is, of course, also possible (and also preferred) to locate the first mixing device at a position above the horizontally operated mixing device in such a way that the mixture obtained in the first mixing device can flow into the product inlet of the horizontally operated mixing device, only driven by gravity. In this case, a drop shaft can be used to guide the mixture into the horizontally operated mixing device. Moreover, it is possible to use pipes by means of which the mixture obtained in the first mixing device can be transferred into the horizontally operated mixing device. The pipes connect the product outlet of the first mixing device and the product inlet of the horizontally operated mixing device.

As the mixture has to be heated in the horizontally operated mixing device for the purpose of crosslinking the surface of the water-absorbent polymer particles, it may also be advantageous to preheat the mixture in a further preheater that is located between the first mixing device and the horizontally operated mixing device. In the preheater the mixture may be preheated from a temperature in the range from 20 to 100° C., preferably from 40 to 60° C. to a temperature in the range from 100 to 160° C., preferably from 120 to 140° C.

Moreover, it may also be advantageous to allow the aqueous crosslinker solution to sufficiently penetrate into the surface area of the water-absorbent polymer particles and to more homogeneously wet the surface of the water-absorbent polymer particles by introducing the mixture into a further dwell time mixer that may also be located between the first mixing device and the horizontally operated mixing device.

At least the horizontally operated mixing device provides means to heat-treat the mixture obtained in process step (x1a). It might have the same geometry as the first mixing device or might be of a different geometry. The mixing device might be of any shape and dimension to achieve an appropriate mixing of the polymers. The cross-sectional geometry of the horizontally operated mixing device might be circled, oval, cylindric or rectangular. The mixing devices provide at least one surface to contact the compound during the heating process. This surface is called the "contacting surface". The horizontally operated mixing device might be of any volume. Preferably the filling volume of this mixing device is in the range from 1 l to 250000 l, more preferably in the range from 100 l to 100000 l, most preferably in the range from 10000 l to 30000 l. Preferably, about 4 to 10 tons per hour, even more preferred 6 to 8.5 tons per hour of the mixture are introduced into the horizontally operated mixing device.

It is preferred to achieve a high degree of mixing the polymer particles and the crosslinker. For this purpose at least a part of the first mixing device or the horizontally operated mixing device or both mixing devices might be moved at least in one direction, preferably in two directions, more preferably in more than two directions. The movement might be horizontally or vertically. The movement of at least a part of the first or second mixing device is preferably a turning or rotating of the movable parts like a shaft that bears paddles (in case of the horizontally operated second mixing device it is a rotation of the paddle shafts(s)). The turning or rotating of at least a part of the first or second mixing device might be established horizontally or vertically or both (in case of the second mixing device it is a horizontal rotation of the paddle shaft(s)). The turning of at least parts of the first mixing device might be established in more than one direction simultaneously or consecutively.

According to a preferred embodiment of the process according to the present invention the horizontally operated mixing device is a so called "paddle dryer". A paddle dryer belongs to the group of indirect heating type dryers that, without using any gas as heating medium, heat powdered materials by direct contact with hollow cuneiform type rotating heaters (paddles which are mounted onto one or more shafts rotating around an axis in a horizontal direction). All or nearly all of heat capacity necessary for drying are brought by the direct heat transfer from the paddle shafts and the jacket. The heat-transfer area of preferred paddle dryers is preferably in the range from 1 to 500 m$^2$, preferably from 80 to 200 m$^2$. The ratio of the surface of the shaft and the paddles to the surface of the jacket area (surface area "shaft+paddles"/surface area "jacket") is preferably ≥1. Examples of suitable paddle dryers are models NPD-1.6W or NPD-14W from Nara Machinery Co., Ltd., Frechen, Germany. Further mixing devices that are suitable for this purpose are the paddle dryers that are available form Komline-Sanderson, Peapack, USA or the paddle dryers that are available from the Royal GMF-Gouda, Waddinxveen, and The Netherland.

According to a particularly preferred embodiment of the process according to the invention the horizontally operated mixing device is operated at least in part continuously. This is realized, for example, in that the water-absorbing polymer particles which have been mixed with the aqueous surface cross-linking solution in the first mixing device are introduced via the inlet in the front top region of the horizontally operated mixing device, flows through the horizontally operated mixing device and then, after a certain dwell time, leaves the horizontally operated mixing device via the outlet at the rear top region. In this context the average dwell time of a water-absorbing polymer particle depends inter alia on the amount of the mixture that is fed per unit time via the inlet, on the volume of the horizontally operated mixing device and on the amount of heat-treated mixture exiting via the outlet per unit time. Regulation of the dwell time can be rendered possible in particular by an adjustable outlet device, in addition to an adjustable inlet device. This outlet device preferably has one ore more adjustable outlet openings. Possible outlet devices are a weir, preferably a vertically adjustable weir, but also cellular wheel sluices, discharge screws, which can be frequency-regulated in particular, or at least two of these.

The horizontally operated mixing device is hydraulically driven. This can be performed by a hydraulic driver or a hydraulic machine which incorporates a hydraulic motor. Hydraulic motors are a common component in a larger hydraulic system. Hydraulic motors convert hydraulic energy into mechanical energy. In industrial hydraulic systems, pumps and motors are typically used in conjunction with proper valves and piping to form a hydraulic powered transmission. Usually, a pump is connected via a carrier line to a motor, which then draws fluid from a reservoir and forces it into the motor. The fluid forces the movable components of the motor into motion, which in turn rotates the attached shaft. The shaft, which is mechanically linked to the work load, provides rotary mechanical motion. Finally, the fluid is discharged at low pressure and transferred back to the pump. As fluids different oils as well as water can be used. The advantage of a hydraulic machine compared to electric motors to advance the horizontally operated mixing device is that the hydraulic machine can convert a high amount of power to the mixing device without the risk of an overrunning or slippage. This has the advantage that even after a stopping of a continuous process where the compound rests in the mixing device a restart can be established easily. For this restart often high amounts of energy have to be applied as the compound often sticks together as it could not be mixed in a regular way.

In a preferred embodiment of the process the mixture is heat-treated at a temperature in the range from 150 to 250° C., more preferred in the range from 160 to 240° C. and most preferred in a range from 170 to 230° C. in the horizontally operated mixing device. The mixture might also be heat-treated in the first mixing device, which then also might be hydraulically driven. The heating of the mixture in one of the mixing devices might be established by heating the contacting surface of the mixing device or by blowing heated gas into the compound. For that reason the mixing device might provide openings at least in parts of the contacting surface.

In the process according to the preset invention the horizontally operated mixing device comprises one or more rotating shafts, preferably one or more rotating paddle shaft, particular preferred two rotating paddle shafts that are rotating in an opposite direction, and a hydraulic motor that converts hydraulic pressure and flow into torque and angular displacement, thereby forcing the paddle shaft into a horizontal rotation. The translation of the hydraulic power to a movement of the shaft is preferably achieved without many transformational parts. In this way the power of the hydraulic motor can be converted without high energy losses to the shaft. Even if the compound is stick in the mixing device because of an interruption of the process, the mixing device can easily be started by the power of the hydraulic motor.

It is preferred that paddles are provided on the rotating shaft. The paddles might be of any geometry and size as long as they support the mixing process. Preferred the paddles have an elongated form. The paddles might preferably be oriented in an angular direction from the contact surface, preferred with an angle in the range of 10° to 90°, preferred in the range of 30° to 70°, more preferred in the range of 40° to 60°. The paddles might comprise any material which is suitable for the contact with the compound. Preferred the paddles comprise a metal, plastic, wood or ceramics or a mixture of at least two of those. Preferably the paddles comprise a metal chosen from the group consisting of iron, in particular high-grade steel, titanium, silver, gold, chromium, cobalt or more than one thereof. Optionally the paddles might be coated with suitable polymers, for example with polypropylene or poly(tetrafluorethylene) polymers. The number of paddles is preferably in a range from 1 to 75, more preferably in a range form 10 to 50 and most preferably in a range from 15 to 30. In the preferred embodiment, in which the horizontally operated mixing device comprises two rotating paddle shafts, the number of paddles n each shaft can differ by one, two or three paddles, preferably by one paddle. Furthermore it is preferred that both, the rotating shaft onto which the paddles are mounted as well as the paddles, have a hollow structure such that that a heating medium can flow through these parts of the mixer as well as through the double-wall blanket of the mixer. Accordingly, the inner surface of the blanket of the horizontally operated mixing device as well as the outer surfaces of the paddles and the shaft serve as the contacting surfaces used to heat the product.

Further it is preferred that oil is used as the hydraulic liquid used in the hydraulic motor. Any hydraulic oil could be used that does nearly not alter its volume when it is pressurized. The oil could be any oil that is fluid in a temperature range from 10° C. to 300° C., preferably in a range from 50° C. to 270° C., most preferably in a range from 100° C. to 250° C.

The hydraulic driver or machine might power the paddle shaft directly or indirectly. A direct power might be established by directly connecting for example a hydraulic arm to the paddle shaft of the horizontally operated mixing device. It is, however, preferred to couple the paddle shaft of the horizontally operated mixing device to the hydraulic motor via one or more cog wheels. These cog wheels may be located within a tank that is filled with a gear oil. In order to prevent that the gear oil decomposes at the temperatures in the horizontally operated mixing device, it is advantageous to cover the surface of the gear oil in the tank with a nitrogen atmosphere, thereby preventing any contact of the hot gear oil with oxygen (which would lead to a decomposition of the gear oil).

Further a process is preferred where the average residence time of a particle in the horizontally operated mixing device is in the range from 5 to 500 minutes, more preferably in a range from 10 to 250 minutes, most preferably in a range from 20 to 180 minutes. During this dwell time the polymer particles that have been mixed with the crosslinker react with the crosslinker on their surfaces such that surface-crosslinked polymer particles re obtained.

A preferred embodiment is when the rotation speed of the shaft in the horizontally operated mixing device is in the range from 5 to 25 rpm, more preferably in a range from 7.5 to 22.5 rpm, most preferably in a range from 10 to 20 rpm.

A contribution to the solution of the objects mentioned at the beginning is also made by water-absorbent polymer particles which are obtainable by such a process. Preferably, these water-absorbent polymer particles are characterized by a residual monomer content of less than 500 ppm, preferably less than 450 ppm and even more preferably of less than 400 ppm, determined according to test method WSP 210.2.

A further contribution to achieving the objects described at the beginning is made by a composite material comprising the water-absorbent polymer particles obtainable by the process according to the present invention and a substrate. In this context, it is preferable for the water-absorbent polymer particles and the substrate to be firmly bonded to one another. Preferred substrates are films of polymers, such as, for example, of polyethylene, polypropylene or polyamide, metals, nonwovens, fluff, tissues, woven fabric, natural or synthetic fibres, or other foams. It is furthermore preferable according to the invention for the composite material to include at least one region which comprises the water-absorbent polymer particles in an amount in the range of from about 15 to 100 wt. %, preferably about 30 to 100 wt. %, particularly preferably from about 50 to 99.99 wt. %, furthermore preferably from about 60 to 99.99 wt. % and moreover preferably from about 70 to 99 wt. %, in each case based on the total weight of the composite material region in question, this region preferably having a size of at least 0.01 $cm^3$, preferably at least 0.1 $cm^3$ and most preferably at least 0.5 $cm^3$.

In a particularly preferred embodiment of the composite material according to the invention, this is a planar composite material such as is described as "absorbent material" in WO 02/056812 A1. The disclosure content of WO 02/056812 A1, in particular with respect to the precise structure of the composite material, the weight per unit area of its constituents and its thickness, is introduced herewith as reference and represents a part of the disclosure of the present invention.

A further contribution to achieving the objects mentioned at the beginning is made by a process for the production of a composite material, wherein the water-absorbent polymer particles obtainable by the process according to the present invention and a substrate and optionally an additive are brought into contact with one another. Substrates which are employed are preferably those substrates which have already been mentioned above in connection with the composite material according to the invention.

A contribution to achieving the objects mentioned at the beginning is also made by a composite material obtainable by the process described above, this composite material preferably having the same properties as the composite material according to the invention described above.

A further contribution to achieving the objects mentioned at the beginning is made by chemical products comprising the water-absorbent polymer particles obtainable by the process according to the present invention or a composite material according to the invention. Preferred chemical products are, in particular, foams, shaped articles, fibres, foils, films, cables, sealing materials, liquid-absorbing hygiene articles, in particular nappies and sanitary towels, carriers for plant or fungal growth-regulating agents or plant protection active compounds, additives for building materials, packaging materials or soil additives.

The use of the water-absorbent polymer particles obtainable by the process according to the present invention or of the composite material according to the present invention in chemical products, preferably in the abovementioned chemical products, in particular in hygiene articles, such as nappies or sanitary towels, and the use of the superabsorber particles as carriers for plant or fungal growth-regulating agents or plant protection active compounds also make a contribution to achieving the abovementioned objects. In the use as a carrier for plant or fungal growth-regulating agents or plant protection active compounds, it is preferable for the plant or fungal growth-regulating agents or plant protection active compounds to be able to be released over a period of time controlled by the carrier.

The invention is now more closely illustrated by figures.

Figure 1:
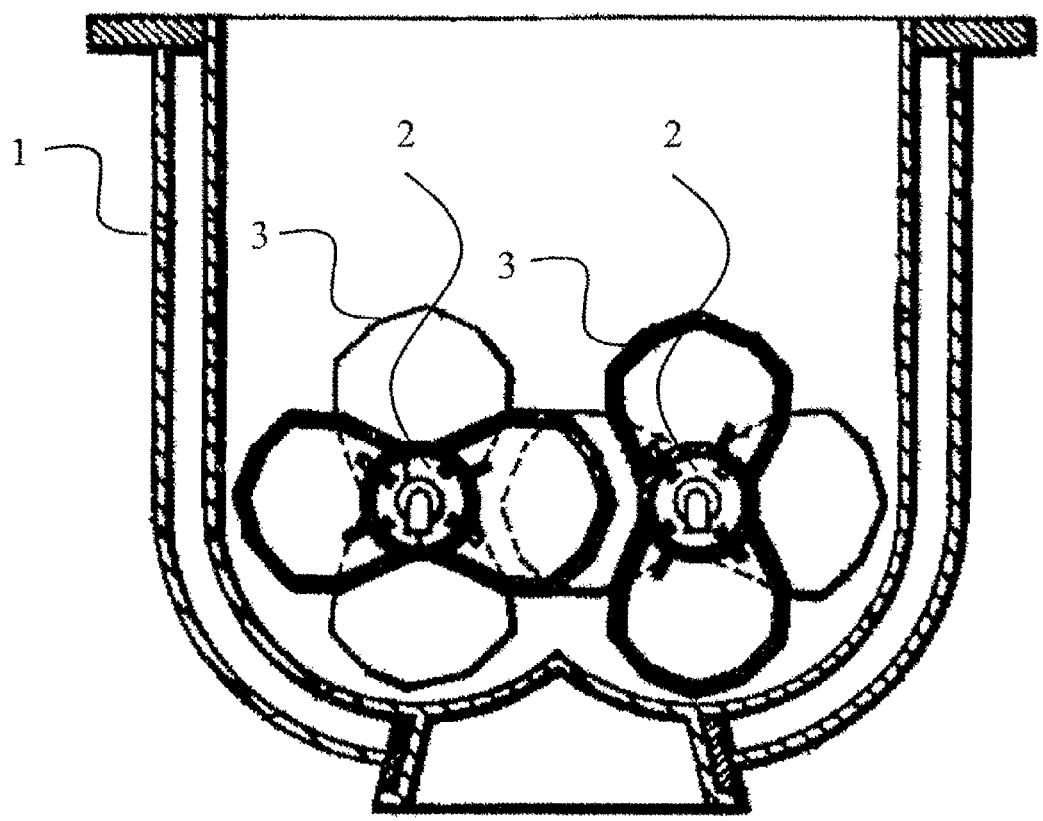
FIG. 1 is a cross-sectional view of a horizontally operated mixing device suitable in the process according to the present invention.
Figure 2:
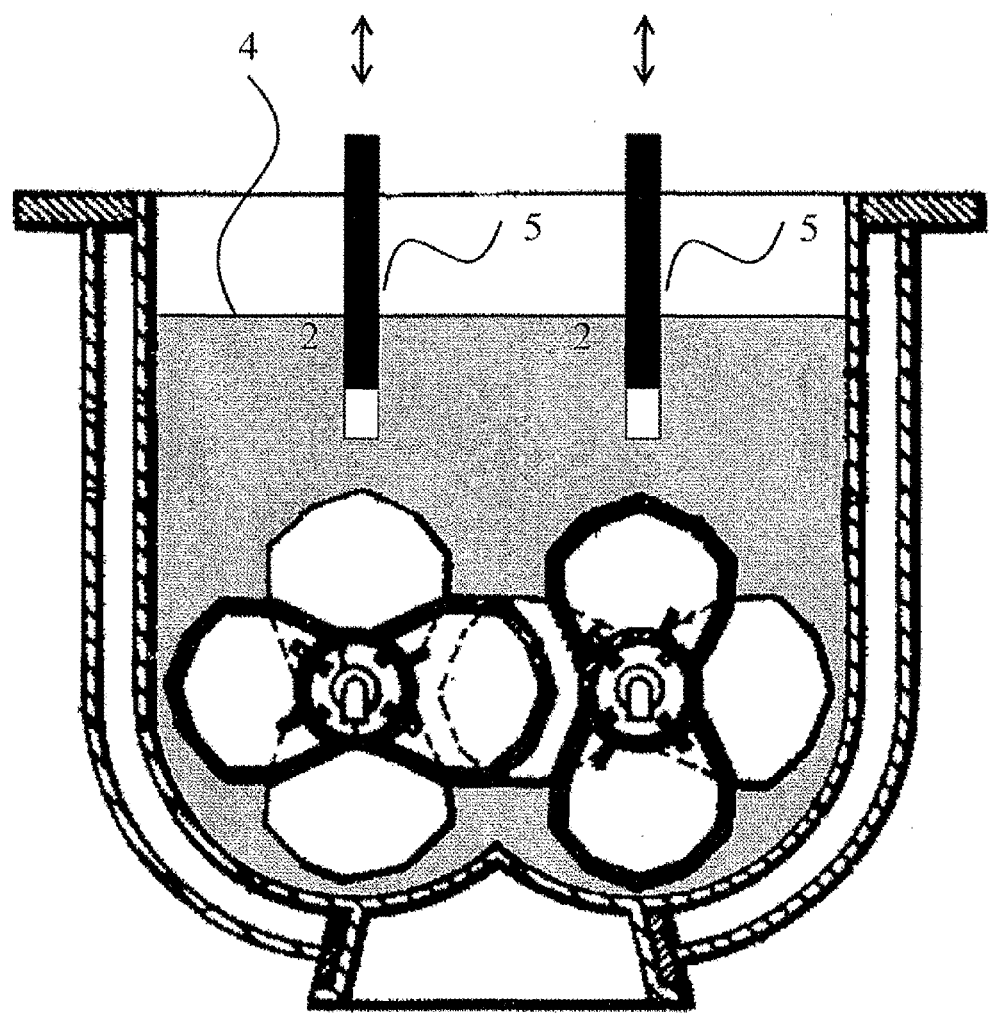
FIG. 2 is a further cross-sectional view of a horizontally operated mixing device suitable in the process according to the present invention.

FIG. 1 shows a cross-sectional view of a horizontally operated mixing device 1 suitable in the process according to the present invention. The mixing device 1 comprises to rotating paddle shafts 2 which are provided with a plurality of mixing paddles 3. As shown in FIG. 2, the filling level 4 within the horizontally operated mixing device 1 and thus the dwell time of the water-absorbent polymer particles within the horizontally operated mixing device 1 can be controlled by an adjustable outlet device. This outlet device preferably has adjustable outlet openings 5 in the form of vertically adjustable weirs.

Figure 3:
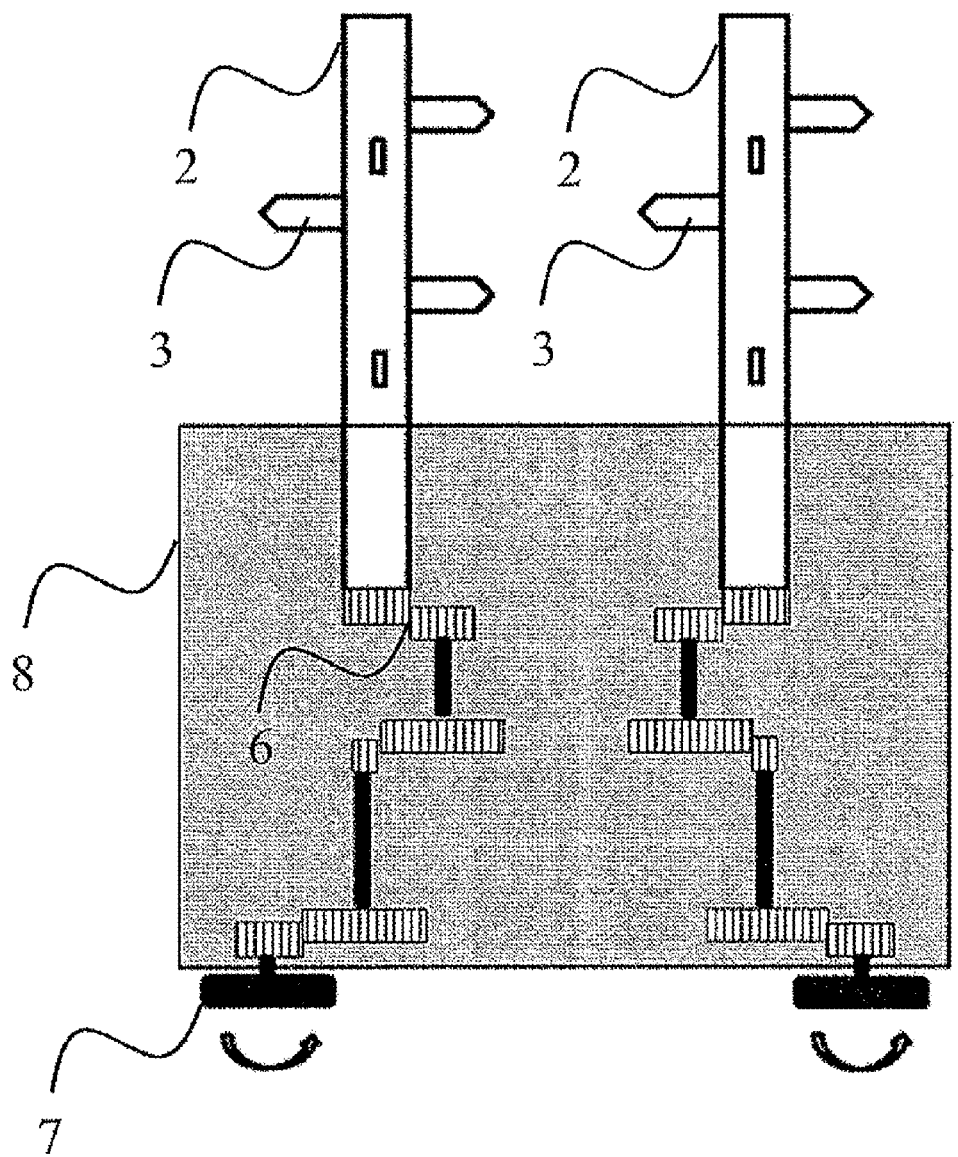
FIG. 3 is a cross-sectional view of a horizontally operated mixing device in which the paddle shafts are driven indirectly by the hydraulic force via cog wheels.

FIG. 3 is a cross-sectional view of a horizontally operated mixing device 1 in which the paddle shafts 2 are driven indirectly by the hydraulic force via cog wheels 6. By means of a hydraulically driven cog wheel 7 that is directly coupled to the hydraulic motor the force is transmitted to the paddle shafts 2 via several cog wheels 6 which are all located in a tank 8. Tank 8 is filled with a gear oil, wherein the gear oil is preferably under a nitrogen atmosphere.

Figure 4:
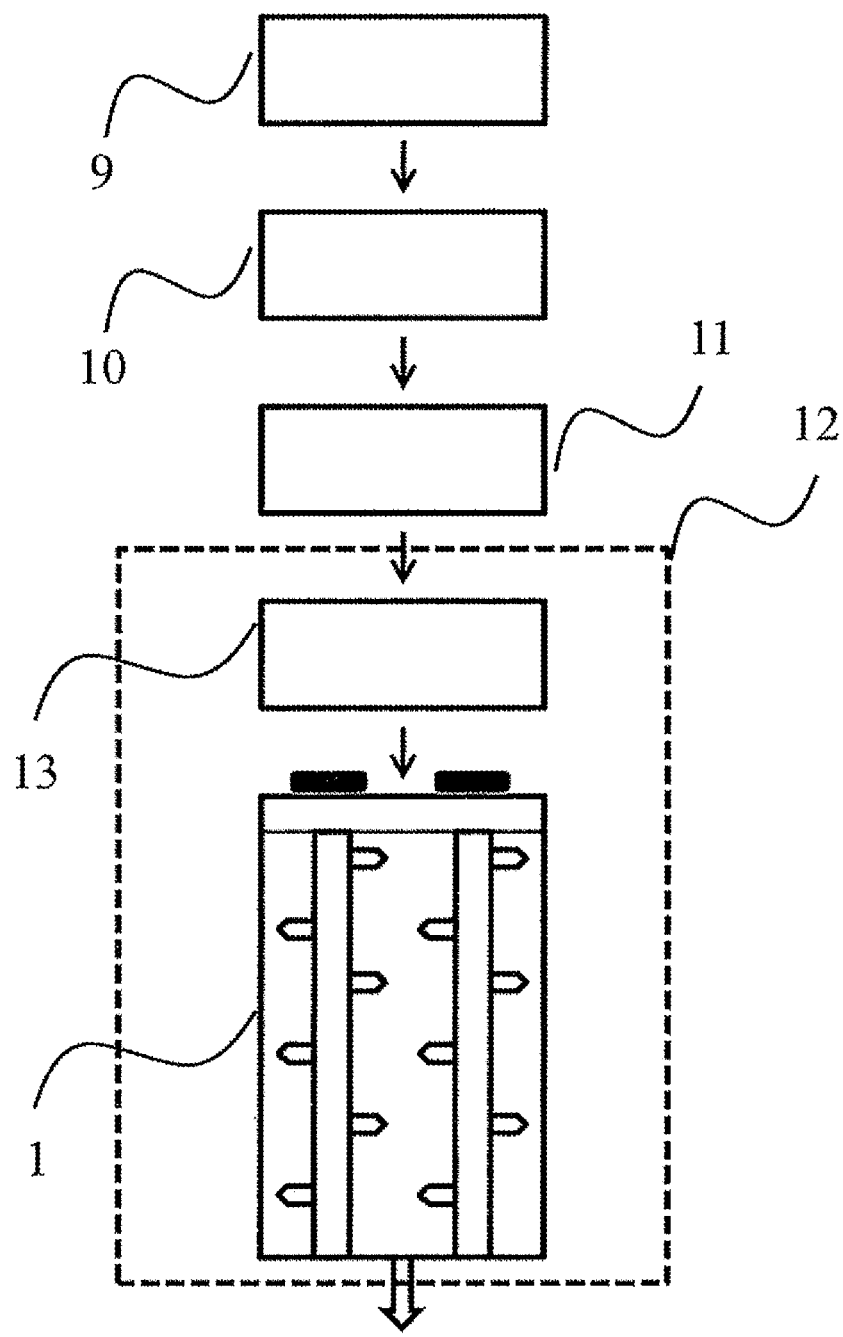
FIG. 4 is a flow chart of the process according to the present invention.

FIG. 4 shows a particular embodiment of the device according to the invention for the production of superabsorbers. In the polymerization region 9 a polymer gel is formed by free-radical polymerization from an aqueous monomer solution comprising partly neutralized acrylic acid, at least one crosslinking agent and initiators, and is then optionally after comminution of the gel, dried in a drying region 10, preferably down to a water content of less than 10 wt. %. The water-absorbing precursor obtained in this manner is then treated in a further grinding and sieving section 11 to obtain a particular particle size fraction.

The thus obtained water-absorbent polymer particles are then transferred into a surface crosslinking section 12 that comprises a first mixing device 13 (which may be a Schugi® mixer, and a horizontally operated mixing device 1 that is hydraulically driven. The horizontally operated mixing device might for example be a Nara® mixer.

LIST OF REFERENCES 1 horizontally operated mixing device
2 shaft
3 paddle
4 filling level
5 adjustable weir
6 cog wheel
7 cog wheel that is directly hydraulically driven
8 tank
9 polymerization region
10 drying region
11 grinding and sieving section
11 surface crosslinking section
13 first mixing device

The invention claimed is:

1. A process for the preparation of water-absorbent polymer particles, comprising the process steps of
preparing an aqueous monomer solution comprising at least partially neutralized, monoethylenically unsaturated monomers bearing carboxylic acid groups (α1) and at least one crosslinker (α3);
adding a polymerization initiator or a at least one component of a polymerization initiator system that comprises two or more components to the aqueous monomer solution;
decreasing the oxygen content of the aqueous monomer solution;
charging the aqueous monomer solution into a polymerization reactor;
polymerizing the monomers in the aqueous monomer solution in the polymerization reactor to form a polymer gel;
discharging the polymer gel out of the polymerization reactor and comminuting the polymer gel thereby obtaining polymer gel particles;
drying the polymer gel particles;
grinding the dried polymer gel particles thereby obtaining particulate water-absorbent polymer particles;
sizing the grinded water-absorbent polymer particles; and
step (xi) crosslinking the surface of the grinded and sized water-absorbent polymer particles;
wherein process step (xi) comprises the steps of:
(x1a) mixing the water-absorbent polymer particles with an aqueous crosslinker solution; and
(x2a) heat-treating the mixture obtained in process step (x1a) in a horizontally operated mixing device,
wherein the horizontally operated mixing device is hydraulically driven.

2. The process according to claim 1, wherein mixture obtained in process step (x1a) is heat-treated at a temperature in the range from 150 to 250° C. in the horizontally operated mixing device.

3. The process according to claim 1, wherein the horizontally operated mixing device comprises at least one rotating shaft and a hydraulic motor that converts hydraulic pressure and flow into torque and angular displacement, thereby forcing the shaft into rotation.

4. The process according to claim 3, wherein at least two paddles are provided on the rotating shafts.

5. The process according to claim 3, wherein an oil is used as the hydraulic liquid used in the hydraulic motor.

6. The process according to claim 1, wherein the average residence time of the water-absorbent polymer particles in the horizontally operated mixing device is in the range from 5 to 500 minutes.

7. The process according to claim 3, wherein the rotation speed of the shaft in the horizontally operated mixing device is in the range from 5 to 25 rpm.

* * * * *

UNITED STATES PATENT AND TRADEMARK OFFICE
CERTIFICATE OF CORRECTION

| | | |
|---|---|---|
| PATENT NO. | : 9,255,190 B2 | Page 1 of 1 |
| APPLICATION NO. | : 14/364525 | |
| DATED | : February 9, 2016 | |
| INVENTOR(S) | : Harald Plochinger et al. | |

It is certified that error appears in the above-identified patent and that said Letters Patent is hereby corrected as shown below:

Title Page, correct the Applicants data in item (71) with the following data:

--Evonik Industries AG, Essen (DE)--

Signed and Sealed this
Third Day of May, 2016

Michelle K. Lee
*Director of the United States Patent and Trademark Office*